United States Patent [19]

Boris et al.

[11] Patent Number: 5,031,797

[45] Date of Patent: Jul. 16, 1991

[54] REAGENT STORAGE AND DELIVERY SYSTEM

[75] Inventors: Michael Boris, Placentia; Richard C. Meyer, La Habra; Robert M. Price, Walnut, all of Calif.

[73] Assignee: Beckman Instruments, Inc., Fullerton, Calif.

[21] Appl. No.: 534,324

[22] Filed: Jun. 4, 1990

Related U.S. Application Data

[63] Continuation of Ser. No. 273,671, Nov. 18, 1988, abandoned, which is a continuation of Ser. No. 892,735, Jul. 30, 1986, abandoned, which is a continuation of Ser. No. 520,885, Aug. 5, 1983, abandoned.

[51] Int. Cl.$^5$ .......................... B67D 5/08; G06K 7/10
[52] U.S. Cl. ........................................ 222/23; 222/52; 222/129; 235/459; 422/102; 73/864.82
[58] Field of Search .................. 222/23, 52, 129, 482, 222/81, 541; 221/87, 88; 73/864.82, 864.84, 864.85, 864.86; 422/65, 102; 235/459, 488; 209/554

[56] References Cited

U.S. PATENT DOCUMENTS

| | | | |
|---|---|---|---|
| 3,388,237 | 6/1968 | Read | 235/494 X |
| 3,502,851 | 3/1970 | Kakimoto et al. | 235/488 |
| 3,553,435 | 1/1971 | Pike | 235/459 |
| 3,612,321 | 10/1971 | Larson | 422/102 |
| 3,612,888 | 10/1971 | Boucher | 235/459 X |
| 3,718,439 | 2/1973 | Rosse et al. | 422/102 |
| 3,916,157 | 10/1975 | Roulette et al. | 235/454 X |
| 3,994,594 | 11/1976 | Sandrock et al. | 422/102 X |
| 4,066,412 | 1/1978 | Johnson et al. | 422/65 |
| 4,085,314 | 4/1978 | Schultz et al. | 235/488 X |
| 4,418,278 | 11/1983 | Mondshein | 235/488 X |
| 4,505,498 | 3/1985 | Weinberger | 235/488 X |

FOREIGN PATENT DOCUMENTS

| | | | |
|---|---|---|---|
| 2393518 | 2/1979 | France | 235/488 |
| 83/00102 | 1/1983 | World Int. Prop. O. | 422/102 |

OTHER PUBLICATIONS

Pearce et al., "Sample Injection Part for High Pressure Chromatography", *Analytical Chemistry*, vol. 44, No. 6 (May 1972), pp. 1107-1109.

*Primary Examiner*—Robert P. Olszewski
*Assistant Examiner*—Steve Reiss
*Attorney, Agent, or Firm*—William H. May; Gary T. Hampson

[57] ABSTRACT

A reagent storage and delivery apparatus comprises a reagent cartridge having a plurality of fluidic chambers and includes a flange means for receiving a label to define a code indicating information concerning the contents of the cartridge. Preferably, a binary code is defined through use of windows formed in an extending portion of the cartridge which cooperate with a formed portion of the label applied to the cartridge. The binary code is optically read and translated to a digital information signal for instructional use with an analytical instrument.

11 Claims, 4 Drawing Sheets

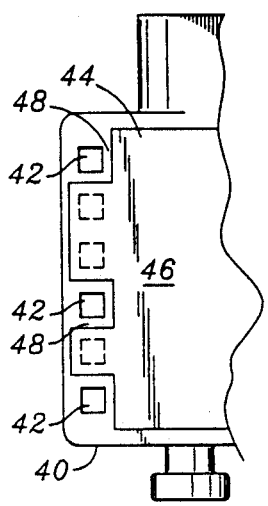
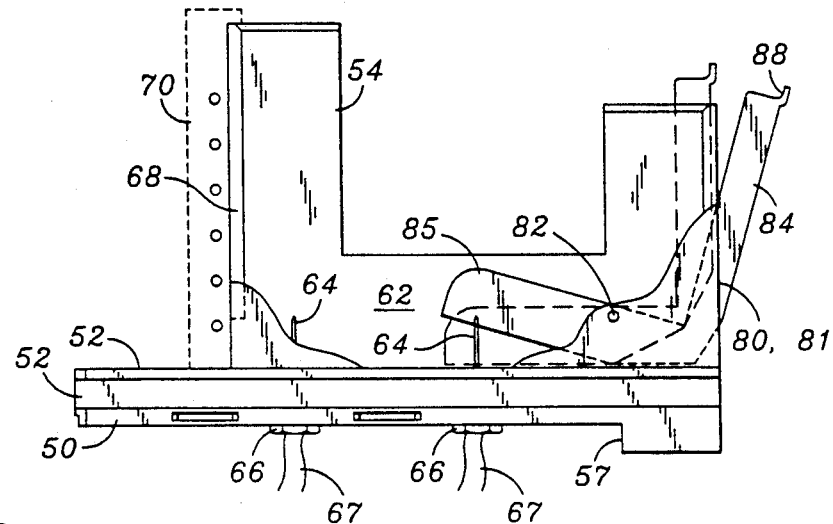
FIG. 2B
FIG. 2C
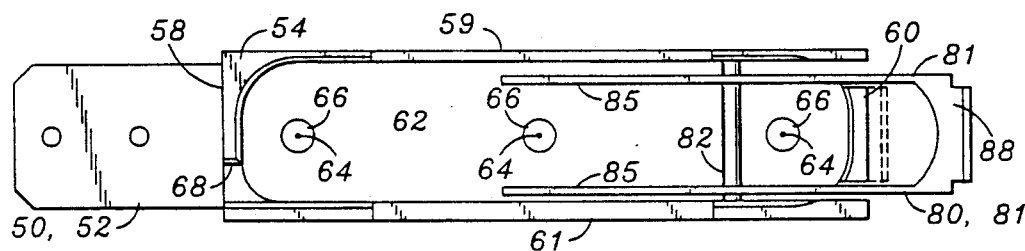
FIG. 3
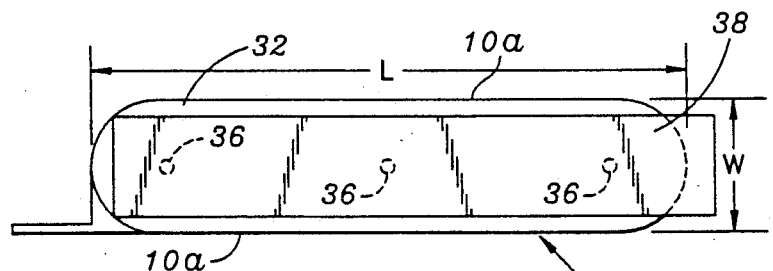
FIG. 4

REAGENT STORAGE AND DELIVERY SYSTEM

This application is a continuation of Ser. No. 07/273,671, filed on Nov. 18, 1988 (now abandoned), which was a continuation of Ser. No. 06/892,735, filed on July 30, 1986 (now abandoned), which was a continuation of Ser. No. 06/520,885, filed on Aug. 5, 1983 (now abandoned).

FIELD OF THE INVENTION

The present invention pertains to reagent storage and delivery means for analytical instruments performing chemical analysis. More specifically, the invention relates to cartridge-type reagent packages and apparatus for receiving such packages to dispense contained reagent to an analytical instrument, including label means for providing information regarding the contained reagent and the analysis desired.

BACKGROUND OF THE INVENTION

Many chemical analyses, particularly those performed to indicate health related problems, require chemical reagents to obtain a desired measurable chemical reaction. Some chemical reactions require use of more than one reagent. Furthermore, neutral diluent solutions and washing solutions may be advantageous to assure correct concentrations of reagents and to prohibit contamination.

In an automated analytical instrument which performs such analyses, it is advantageous to provide all the necessary reagent solutions for the analytical instrument in prepackaged or cartridge form so that fluid exposure and possible spillage near the instrument may be prevented. Furthermore, cartridge type reagent containers permit fast and easy attachment of a reagent container to the instrument.

Prior means and methods in supplying reagent to an analysis instrument have shown a need for reagent packages in which complementary types of reagents are individually contained in one cartridge. Thus, a benefit may be provided for an analysis instrument which uses mixtures of individual reagents and diluents, by combining the chemicals necessary in a singular cartridge. Furthermore, for those analyses which require calibration, a calibrator may be included in the package along with reagent for analysis, so that all the chemicals necessary for performing an analysis are contained in a singular package.

It is also necessary to provide information regarding the reagent contained in any selected package. It has been learned that automated information systems may be utilized which read information directly from a package regarding its contents. Many bar code and other marking systems have been used from which information may be obtained regarding a contained substance. Often, however, simple inclusion of a information on a label applied to the cartridge severely handicaps accessability to an information source for reading. The need thus remains present for supplying information to an instrument receiving a fluid container which permits easy access to the information and which advantageously utilizes label controls and inspections used in manufacturing and packaging processes to assure that the information provided accurately indicates the substance contained.

SUMMARY OF THE INVENTION

The present invention comprises a cartridge for storing and dispensing chemical reagents, an apparatus for receiving the reagent cartridge, and apparatus for encoding and communicating information regarding the reagent and related tests using the reagent to instruct an analytical instrument.

The reagent cartridge embodies multiple chambers for holding individually selected fluidic reagents or chemicals. The cartridge is adapted for easy insertion into and withdrawal from a receiving apparatus to dispense contained reagent. Each chamber is provided with an entry port having a resealable sealing means for receiving a probe to remove its contents, and with a vent means sealed for storage which may be opened to vent removal of the contents.

The reagent cartridge is provided with a means for communicating information to an analytical instrument concerning the reagent composition and quantity, and the chemical analysis selected. Said means comprises a fixed portion of the cartridge body which cooperates with a label for the cartridge having a permutable portion to define a readable instruction table from which a digital code may be obtained which indicates the desired information of the reagent and related chemical tests. Additionally, a means for electronically reading the instruction table defined by the cartridge and label is provided so that information contained in the digitized code may be processed and provided to the analysis instrument.

A receiving apparatus for receiving the reagent cartridge comprises a structure having a receiving space which closely approximates the shape of the reagent cartridge. The receiving apparatus is adapted to properly and quickly guide a cartridge into alignment for insertion into the apparatus. A plurality of fluidic probes are provided which extend into the receiving space to transfix the sealing elements sealing the entry ports of the cartridge chambers. The probes enter into the chambers of the cartridge when the cartridge is inserted into the receiving apparatus. The rapid aligning ability to rapidly align the cartridge with the receiving space due to cooperation of the shape of the cartridge and the receiving apparatus assure correct insertion of the cartridge for entry of the probes into the chambers of the cartridge.

A means for ejecting the cartridge to dislodge the cartridge from the probes and receiving apparatus is provided for fast and easy removal of the cartridge.

DESCRIPTION OF THE DRAWINGS

FIG. 2, comprising FIGS. 2A, 2B and 2C, is an illustration of a reagent cartridge and a receiver for the cartridge, with the reagent cartridge aligned for insertion into the receiver. A partial section of the reagent cartridge (FIG. 2A) illustrates the individual chambers contained within the cartridge and the structure of the resealable sealing element.

FIG. 2B illustrates the reagent cartridge with a label having a differently configured end portion. A partial section of the receiving apparatus (FIG. 2C) illustrates the probes for entering the reagent cartridge and a means for ejection of the reagent cartridge for removal.

FIG. 3 is a top view of the receiving apparatus.

FIG. 4 is a top view of the reagent cartridge illustrating means for unsealing the vent openings.

DESCRIPTION OF THE BEST MODE

Figure 1:
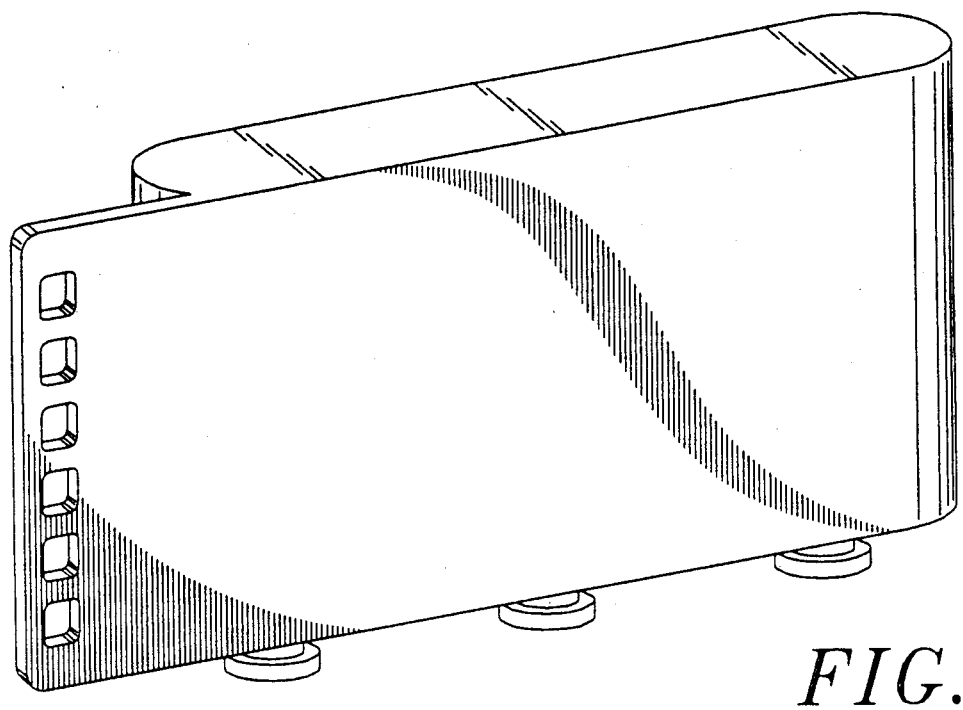
FIG. 1 is a perspective view of a reagent cartridge embodying the features described in the present application.
Figure 2A:
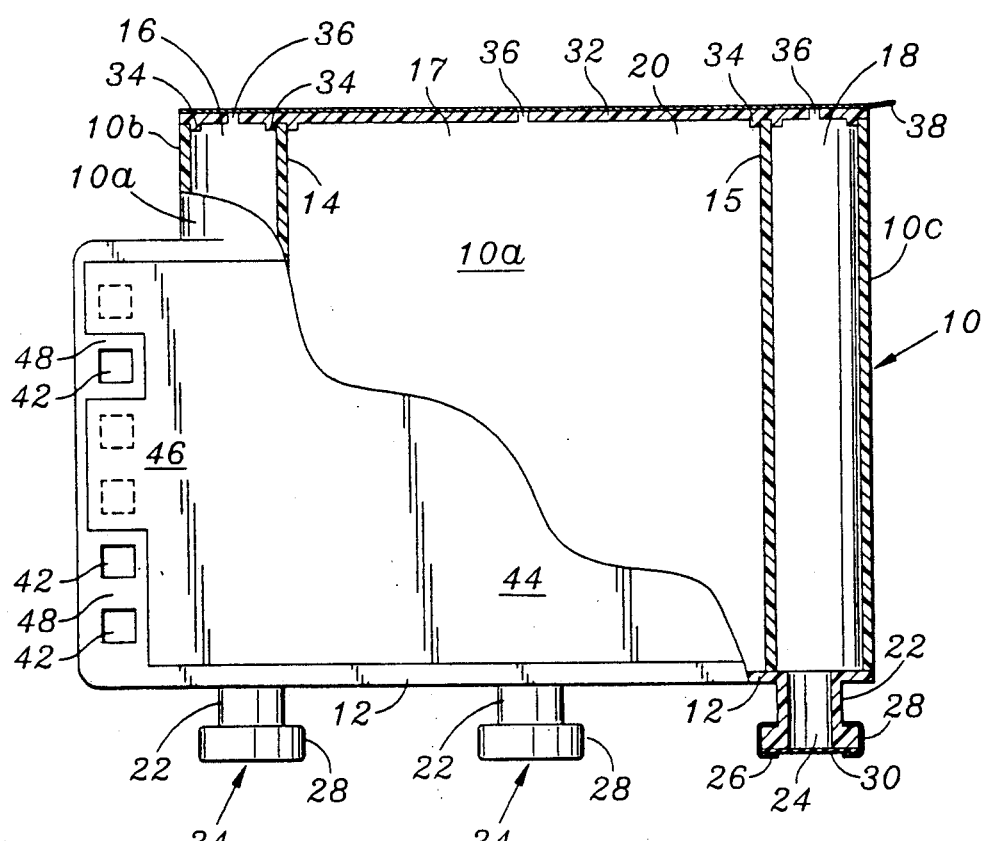

Referring to FIGS. 1, 2 and 4, a reagent cartridge embodying the elements of the present invention may be described. The cartridge comprises a vertical exterior wall 10 defining an interior space 20. The wall 10 has separated elongate side portions 10a and rounded opposing end portions 10b and 10c. The defined interior space 20 has a length L much greater than width W. In the described embodiment, the ratio between length and width is approximately 5 to 1, however, many other proportions may be used to adapt a reagent cartridge to the space constraints defined by the analysis instrument with which it will be used.

A floor 12 closes the bottom of the interior space 20 defined by the wall 10. Dividing walls 14 and 15 extend vertically from the floor 12 between the side portions 10 to separate the interior space 20 into three individual chambers 16, 17 and 18 for holding individual reagents. Preferably, the central chamber 17 is given a larger volume (for example 110 cubic centimeters) than the adjacent chambers 16 and 18 (for example 20 cubic centimeters) so that the cartridge may supply varying volumes of differing reagents as required in a selected analytical chemistry test.

A plurality of necks 22 extend from the floor 12, each neck 22 having a centrally located entry port 24 which communicates with a chamber 16, 17 or 18 within the cartridge. One neck 22 defining an entry port 24 is provided for each chamber 16, 17 or 18. Each neck has a rim 26 circumferentially formed around its extended end to receive a crimping band 28. The band 28 holds an elastomeric sealing element 30 or septum, in sealing engagement with the end of each neck 22 to close the entry port 24 and provide a leakfree fluidic seal for its respective chamber 16, 17 or 18. The elastomeric sealing element is preferably made of TEFLON barrier faced rubber identified as composition No. 541-RED of the West Company.

The exterior wall 10, floor 12, dividing walls).4 and 15, and necks 22 are preferably constructed of a one piece manufacture by molding or casting construction techniques. The cartridge may be constructed of plastic material, or the like, which is chemically inert and unreactive with the reagent which the cartridge may contain. It is also preferred that the material of which the cartridge is constructed have resistance to light transmission, particularly ultraviolet light wavelengths, to assure that photometrically sensitive reagents are protected in storage. Such a material, found by Applicant, is known as BAREX, and is available from Standard Oil of Ohio, Vistron Division, and includes pigment identified as amber concentrate 14703-R3 manufactured by Americhem Company.

A cap 32 defined in shape corresponding to the cross sectional shape of the wall 10 of the cartridge, is provided to close the top of the interior space 20 defined by the cartridge wall 10. The cap 32 is provided with a downwardly extending marginal ridge 34 formed around the underside of the cap 32, and spaced from the edge of the cap by a selected distance which generally corresponds to the width of the wall 10. The ridge 34 provides a guide for locating the cap 32 in alignment with the end of the exterior wall 10 of the cartridge, and assists in providing a leak-proof fluidic seal between the cap 32 and the wall 10. Similar ridge members 34 extend laterally along the underside of the cup 32 and are provided to embrace the top of each dividing wall 14 and 15 centrally located in the cartridge between the sidewalls 10. Ridge members 34 similarly provide for alignment of the cap 32 and fluidic seal between the chambers 16, 17 and 18 defined by the dividing walls 14 and 15. The cap 32 is fastened to the exterior wall 10 and the dividing walls 14 and 15 of the cartridge by an ultrasonic welding or by adhesive fastening techniques, as are commonly known for joining plastic-type materials.

A plurality of vent openings 36 are bored through the cap 32 to communicate with chambers 16, 17 and 18 defined within the cartridge. The vent openings 36 vent withdrawal of reagents contained within the cartridge. Generally, one vent opening 36 is provided for each individual chamber 16, 17 or 18. More may be provided as required for adequate venting of fluid removal from the cartridge. A sealing tape 38 is applied to the exterior surface of the cap 32 to seal the vent openings 36 for storage of the reagents in the cartridge. The sealing tape 38 is removed to permit venting of the compartments 16, 17 and 18 when dispensement of reagent is desired. The sealing tape 38 generally comprises an aluminum and/or mylar plastic material having an adhesive applied to one side for adherence to the surface of the cap. A sealing tape as used is available from The 3M Company of St. Paul, Minn. under product number YR 7575 as the product number of the sealing tape therein referred.

The material thicknesses of the exterior wall 10, floor 12, dividing walls 14 and 15, and cap 32 are generally uniform and sized as necessary, depending on the material used, to provide strength and stability to the cartridge.

A flange 40 extends longitudinally outwardly from one end of the reagent cartridge along a plane parallel with the side portions 10a of the cartridge. The flange 40 is substantially flat and is tangent to one sidewall 10a to provide an extended flat surface along one side of the cartridge. This extended flat surface provides a place upon which a label having adhesive backing may be applied. The flange 40 comprises a plurality of vertically aligned windows 42 which provide openings used to generate a digital information signal. In this regard, the outwardly extending position of the flange 40, longitudinally from the end of the cartridge, positions the windows 42 for access to a means for reading a binary code defined thereby.

The label 44 applied to the side of the cartridge displays writing identifying the identity, manufacture, and other qualitative and quantitative information of the reagent. The label 44 also has an end portion 46 which is formed to cooperate with the windows 42 in the flange 40 to define the binary code. In this regard, the end portion 46 of the label 44 selectively covers windows 42 in the flange 40. Remaining windows 42 formed through the flange 40 are exposed as determined by selected notches 48 formed into an edge of the label. The notches 48 may be selected to determine which of the windows 42 formed in the flange 40 are open, and determine which of the windows 42 formed in the flange 40 are covered by the label 44 and closed. The selection of open and closed windows is used to define the binary code from which a digital signal is generated possessing qualitative and quantitative information concerning the reagent contained in the cartridge and related chemical tests. For instance, a series array of optical signal systems, corresponding in position and spacing to the rows of windows 42 formed in flange 40, may be used to direct beams of light through the windows 42 to obtain the information desired. Those windows 42 which are covered with a portion of the label will block the beam of light preventing a signal responsive to that window of the group from being generated. Conversely, a window 42 which is exposed by a notch 48 in the edge of the label 44, will pass a beam of light allowing a signal to be generated for that window of the window group. The combined group of signals generated by of the optical systems responsive to all of the windows 42, provides a binary code from which a digital signal may be generated and utilized to indicate information.

The label 44 material may comprise a foil or other light opaque component to assure that windows 42 covered by portions of the label 44 prevent transmission of light therethrough.

Preferably, six windows 42 are formed through the flange 40 extending from the cartridge, providing six bits of binary code having 64 possible digital signal combinations which may be utilized to communicate information. The preferred utilization of the binary code combinations will be discussed later.

Using a selective shape of the label 44 in cooperation with a portion of a reagent cartridge to define the binary code providing an identification of and qualitative and quantitative information of the reagent and tests to which it pertains, provides a greatly increased measure of assurance that correct and valid usage of the reagent will be obtained. Since the binary code is produced by reading the flange and label combination to determine which of the group of windows are uncovered or open, the label content and placement determine an essential element of the code definition. Thus, using automated packaging methods in which label control and inspection incorporates strict scrutiny of the label content and application on each package, a greater degree of reliability in the information is provided of the reagent results. Combined with the automated reading procedures for the code which directly inform an analysis instrument of the received information, and the fact that the selectively shaped label which is permanently affixed to a cartridge containing the subject reagent, the cartridge is particularly advantageous in verifying accuracy of analysis using the chemical reagents, especially where such analysis is related to human health care.

The receiver for the reagent cartridge is illustrated in FIGS. 2, 3, 5 and 6. The receiver comprises a horizontal frame 50. The frame 50 has a flat top surface 52 for receiving a sidewall structure 54. The sidewall structure 54 is fastened to the top surface 52 of the frame 50 by suitable fastening means. A pair of guideways 56 are formed on opposing sides of the frame 50 to receive rails (not shown) for guiding the receiver for horizontal sliding movement relative to an analysis instrument in which it is carried. A pair of tabs 57 extend downwardly from the frame 50 on each side, to provide a stop for limiting horizontal movement of the receiver into the instrument.

The sidewall structure 54 is comprised of four walls 58, 59, 60, 61 which are interconnected at a lower portion of the structure 54. The structure 54 has an open bottom end closed by the frame 50. An interior space 62 formed by the four walls 58-61, closely approximates the exterior shape of the reagent cartridge, as shown through comparison of FIGS. 3 and 4. The four walls 58-61 thus provide a precision guide for insertion of the reagent cartridge into the interior space 62 of the receiver.

Three probes 64 extend upwardly through the frame 50 and into the space 62 defined by the sidewall structure 54. The tips of the probes 64 protrude sufficiently into the space 62 for entry into an entry port 24 of the reagent cartridge, when the cartridge is inserted into the receiver. The probes 64 preferably comprise non-coring hollow needles which may easily penetrate the elastomeric sealing elements 30, or septums, fastened over each of the entry ports 24, without damaging the sealing elements so that the seal may be reformed for each of the chambers 16-18 if the cartridge is removed from the receiver. Advantageously, each of the probes 64 has a nut and male threaded portion 66 constructed on one end so that the probes 64 may be easily screwed into a threaded bore (not shown) machined through the frame 50. Flow tubes 67 are connected to each of the probes 64, to flow reagent from the chambers 16-18 of the cartridge to the analysis instrument.

An ejector 80 is provided for forcibly removing the reagent cartridge from the receiver and disengaging the entry ports 24 and sealing elements 30 from the probes 64. The ejector 80 comprises an L-shaped lever 81 which is movable about a pivot 82 provided by a shaft inserted through opposing sidewalls 59 and 61 of the sidewall structure 54 and the ejector 80. When a first portion 84 of the L-shaped lever 81 is pulled outwardly and downwardly, the lever 81 moves about the pivot 82 to raise a second portion 85 of the lever 81 upwardly engaging the floor 12 of an inserted cartridge and forcing the cartridge upwardly and out of the receiver.

When the cartridge is inserted into the receiver, the lever 81 resides in a rest position (indicated in FIG. 2 by broken lines) with the second portion 85 of the lever 81 extending below the floor 12 of the cartridge and the first portion 84 of the lever 81 extending upwardly and parallel to end 61 of the sidewall structure 54.

Preferably, two such levers 81 are provided, one each adjacent to the sidewalls 59 and 61, respectively, such that a lever will engage each side of the floor 12 of the cartridge for removal. The levers 81 in pair may be tied for uniform . movement by a connecting portion 88 formed between the two levers 81 such as at the top of the first portions 84 of each lever. Thus, as the lever is moved by exertion of force on the ends of the first portions 84 through the connecting portion 80, both second portions 85 of the lever 81 will simultaneously engage the floor 12 of the cartridge to uniformly urge it upwardly and out of the receiver.

Figure 5:
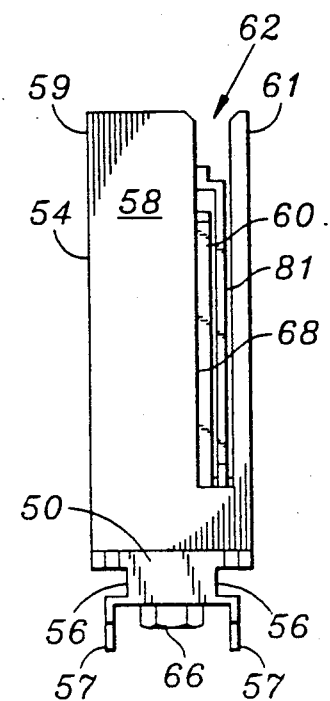
FIG. 5 is an end view of a first end of the receiver.
Figure 6:
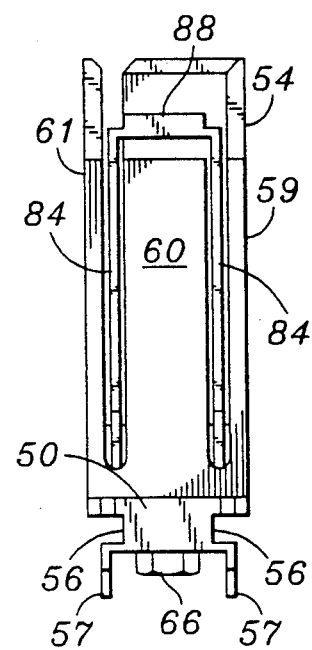
FIG. 6 is an end view of the second opposing end of a receiver.
Figure 7:
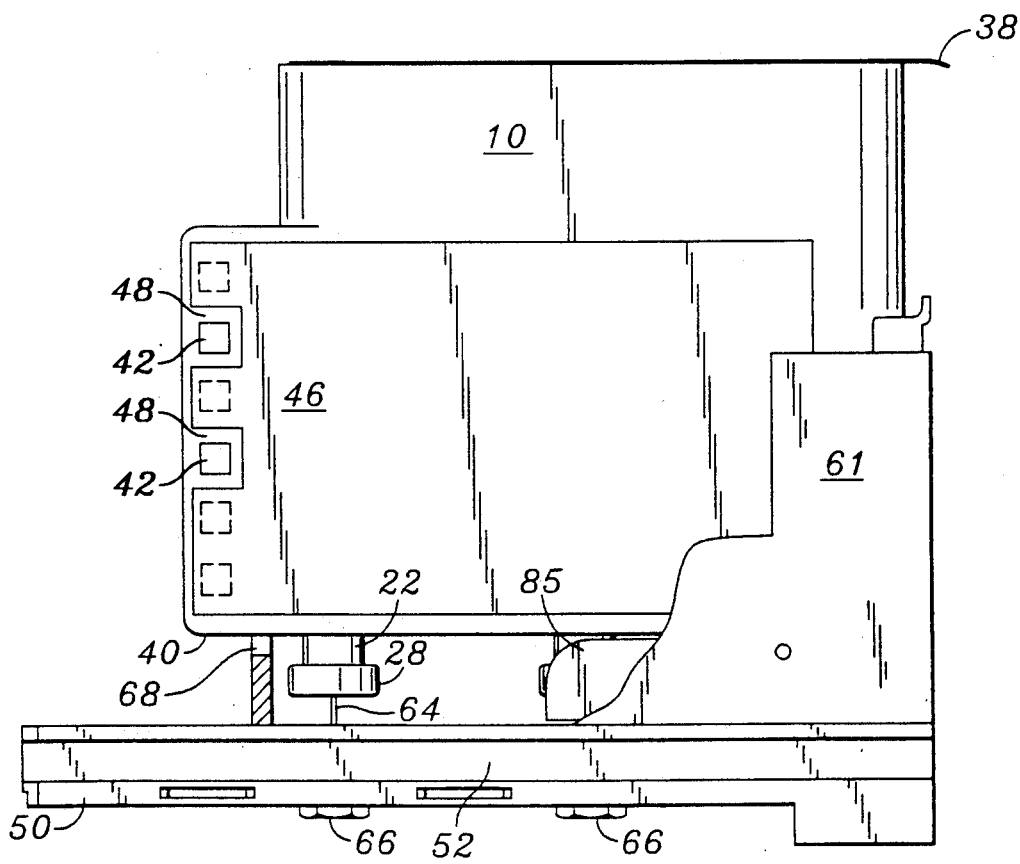
FIG. 7 is a side view of the receiver apparatus having a reagent cartridge inserted for dispensement of reagent.

Referring to FIGS. 3 and 5, a slot 68 is formed vertically through one end of the wall 58 of the sidewall structure 54 to receive the flange 40 extending from the reagent cartridge. When the cartridge is inserted into the interior space 62 of the receiver, the flange 40 extends through the slot 68 permitting the windows 42 formed through the flange 40 to be exposed for communication with a means for reading the information contained thereon, as shown in FIG. 7. A means for reading the information provided by the cooperative relationship of flange 40 and label 44 of the cartridge comprises a series array of infrared light sources and detectors which are mounted in relation to the frame 50 by mounting means (not shown).

Figure 8:
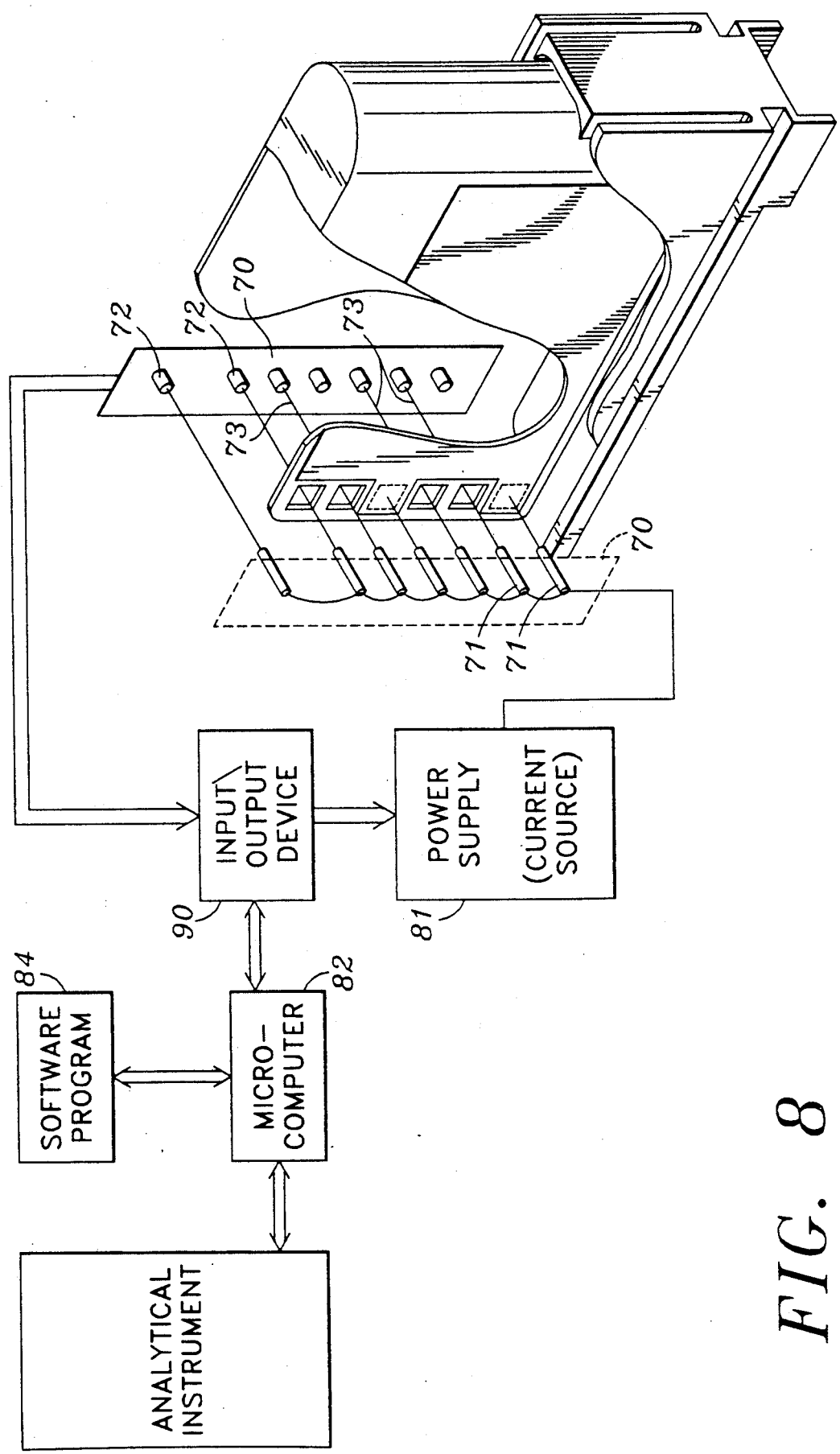
FIG. 8 is a schematic view of the electronic system which obtains and transfers information from the reagent cartridge and label.

The operation of the reagent delivery system may now be described. Referring to FIG. 2 and 8, a reagent cartridge is held in position above the receiver and moved downwardly for insertion into the space 62 formed by the sidewall structure 54 of the receiver. As the cartridge is inserted into the receiver, the sidewalls 58–61 of the receiver engage the sides 10 of the cartridge and precisely guide the cartridge into inserted position. As the cartridge is lowered, the probes 64 transfix the sealing elements 30 of the entry ports 24, and enter the respective chambers 16–18 within the reagent cartridge. The flange 40 displaying the windows 42 enters the slot 68 in the endwall 58 of the receiver and descends between the light sources 71 and light detectors 72 of the array 70 until it is fully positioned therebetween. An uppermost light source 71 and detector 72 of the array 70 form a light bridge above the flange 40 and generates a signal when the cartridge has been completely inserted into the receiver. The ejection lever 81 resides in rest position with the second portion 85 of the lever 81 extending below the floor 12 of the cartridge. The sealing tape 38 is now removed from the cap 32 of the cartridge and the receiver is slidably moved into the instrument. The cartridge and receiver assembly have obtained the configuration of FIG. 7.

With each of the chambers 16–18 transfixed by a probe 64, the reagent may now be withdrawn through the tubes 67 as selected by the analytical instrument. The light bridges formed through exposed or open windows 42 in the flange 40 generate a signal which is applied to a microcomputer to indicate qualitative and quantitative data of the reagent in the cartridge, and tests to be performed.

When the reagent in the cartridge has been used, or other tests using different reagents are desired, the reagent cartridge may be removed by sliding the receiver out of the instrument and by applying pressure to the ejection levers 81. Pressure is applied to the first portion 84 of the ejection levers 81 forcing the first portion 84 downwardly and outwardly from the endwall 60, and thus pivoting the second portion 85 upwardly to engage the floor 12 of the reagent cartridge. Continued pressure forces the cartridge upwardly and out of the receiver disengaging the probes 64 from their mated entry ports 24 and sealing elements 30. As the cartridge is removed, the sealing elements 30 reform a seal preventing leakage of any reagent within a chamber of 16–18 out of the cartridge. The cartridge may then be stored for use at a later time if sufficient reagent remains in the cartridge. For storage, a new strip of sealing tape 38 will be applied in cover the vent openings 36 to the cap 32 of the container.

Referring to FIG. 8, the structure and operation of the means for communicating information concerning the reagent and related test parameters may be described. Light sources 71 and detectors 72 of array 70 are linearly positioned in opposing relationship to provide a series of optical systems or light bridges, indicated as 73, which may be formed through open windows 42 of the flange 40. The array 70 is positioned in parallel relationship with and spaced from the endwall 58 of sidewall structure 54 so that the array 70 is in alignment with the positions of the windows 42 of the flange 40 when the cartridge is inserted in the receiver.

The array 70 comprises seven individual light bridges 73, each comprising an infrared light source 71 and an infrared light detector 72 positioned as described in opposing relationship. When the cartridge is in inserted position, six of the light bridges apply a light beam to a window 42 of the flange 40 and pass the beam of light through the window to be detected if the window is open, i.e. if a label has not blocked the window. Alternatively, the beam of light will be blocked if a portion of the label is covering a window 42 preventing transmission of light therethrough.

The array 70 additionally comprises a seventh light source 71 and detector 72 positioned to form a light bridge above the flange 40 when the cartridge is fully inserted into the receiver. If the cartridge is not completely inserted in the receiver, the flange 40 will block formation of the light bridge, i.e. the beam of light between the source and detector, and thus provide no detector output signal indicating that the cartridge has been completely inserted.

Formation of a light bridge in the detector array between a light source 71 and detector 72 results in an output signal from a responsive detector which provides a signal elemental to determination of the binary code. An output received from detector 72 thus indicates that a window 42 through which the source detector pair is focused is open, i.e. is not covered by a portion of the label 44. Thus, as described, by selectively forming notches 48 in the edge of the label 44 selective signals may be generated by detector 72 by the formation of light bridges in response to those windows permitted to be open. The responses or signals of each source detector pair 71-72 collectively forms a binary code which may be applied to an input output device 90 to generate a digital signal which is communicated to a microcomputer 82. The input/output device 90 adapts current based detector signals to voltage signals so as to be compatible with the microcomputer 82. Such techniques are commonly known and are considered to be supportive of the invention described herein.

The digital signal received by the microcomputer 82 is read through application of a software program 84 programmed into the computer to translate the information provided in the signal into instructions for the analytical instrument which the microcomputer controls and to perform validity tests on the analysis results which the analytical instrument provides. An instrument capable of performing the described processing functions could be an ASTRA ™ Analyzer manufactured by Beckman Instruments, Inc. These operations may also be performed by commonly known methods. The infrared light sources 71 are fired by a current source type power supply 81 which is directed through input/output device 90 by microcomputer 82.

Each of the elements of the array and computer system including the light source 71, light detector 72, power supply 81, input/output device 90 and microcomputer 82 are generally known to those skilled in the art and need not be specifically described. Each is commercially available from many sources and may be easily obtained and combined to form the described system by known techniques.

The software program instructs the microcomputer to translate the digital signal received from the input device into information required by the analytical instrument. The digital signal received is comprised of six bits of information, each bit responsive to one of the source detector pairs 71-72 of the array 70, or in other words, to one of the group of windows 42 on the reagent cartridge. As discussed, the six bit binary code can provide up to 64 individual signals which may be used to indicate specific information regarding the reagent contained in the cartridge and related tests.

In the preferred embodiment, the software program instructs the microcomputer to interpret the digital signals received as is now described. For ease of explanation, the code bits will be referred to by identifying symbols B0 through B5, each identifying a specific bit of the binary code generated by the optical array 70 in response to the open or closed condition of one of the six windows 42 through the flange 40 of the reagent cartridge. Two of the bits designated as B5 and B4 are used to identify the volumetric capacity of the reagent cartridge. The bits identified as B0, B1, B2 and B3 are used to identify the type of chemical analysis to be performed or the composition of the reagent contained within the cartridge. For description of the interpretation of binary code defined by the cartridge, a 0 indicates that no light bridge has been formed or the window 42 is covered with a tab formed on the end of the label 44, and a 1 indicates that a light bridge has been formed and that a window has been exposed by a notch 48 formed in the end of the label 44.

The following informational translations are obtained from bits B5 and B4 of the digital signal supplied to the microcomputer 82, and are explained below in chart form:

| B5 | B4 | Meaning |
|----|----|---------|
| 0 | 0 | Reagent volume in cartridge for 50 tests |
| 0 | 1 | Reagent volume in cartridge for 100 tests |
| 1 | 0 | Reagent volume in cartridge for 250 tests |
| 1 | 1 | Special cartridge containing a fluid other than reagent |

Bits B5 and B4 indicate the volume of the reagent cartridge or that the cartridge is "special" containing no reagent for performing analysis. If bits B5 and B4 are presented in one of the first three combinations, the software program instructs the microcomputer to translate the remaining four bits to determined which chemistry is to be performed or reagent is contained in the cartridge. The translation of the remaining four bits is as follows, shown in chart form:

| B3 | B2 | B1 | B0 | Chemistry |
|----|----|----|----|-----------|
| 0 | 0 | 0 | 0 | None |
| 0 | 0 | 0 | 1 | Aspartate Amino Transferase (AST) |
| 0 | 0 | 1 | 0 | Alanine Amino Transferase (ALT) |
| 0 | 0 | 1 | 1 | Creatine Kinase (CK) |
| 0 | 1 | 0 | 0 | Lactate Dehydrogenase (LD) |
| 0 | 1 | 0 | 1 | LDP |
| 0 | 1 | 1 | 0 | Alkaline Phosphotase (AP) |
| 0 | 1 | 1 | 1 | Gamma Glutamyl Transferase (GGT) |
| 1 | 0 | 0 | 0 | Uric Acid |
| 1 | 0 | 0 | 1 | Triglycerides |
| 1 | 0 | 1 | 0 | Undefined |
| 1 | 0 | 1 | 1 | Cholesterol |
| 1 | 1 | 0 | 0 | Undefined |
| 1 | 1 | 0 | 1 | Undefined |
| 1 | 1 | 1 | 0 | Undefined |
| 1 | 1 | 1 | 1 | Undefined |

If bits B4 and B5 indicate that the reagent cartridge is a special type cartridge such as containing a cleaning fluid or containing undefined chemicals, the software program will instruct the microcomputer to translate the remaining four bits B3 through B0 as follows, in chart form:

| B3 | B2 | B1 | B0 | Cartridge Type |
|----|----|----|----|----------------|
| 0 | 0 | 0 | 0 | None |
| 0 | 0 | 0 | 1 | Universal cartridge |
| 0 | 0 | 1 | 0 | Cleaner |
| 0 | 0 | 1 | 1 | Neutralizer |
| 0 | 1 | 0 | 0 | Diluent for dye test |
| 0 | 1 | 0 | 1 | Undefined |
| 0 | 1 | 1 | 0 | Undefined |
| 0 | 1 | 1 | 1 | Undefined |
| 1 | 0 | 0 | 0 | Undefined |
| 1 | 0 | 0 | 1 | Undefined |
| 1 | 0 | 1 | 0 | Undefined |
| 1 | 0 | 1 | 1 | Undefined |
| 1 | 1 | 0 | 0 | Undefined |
| 1 | 1 | 0 | 1 | Undefined |
| 1 | 1 | 1 | 1 | Undefined |

In all of the above translations, those binary codes which refer to undefined information, may be programmed in the future to refer to specific parameters by modifications to the software program as is required for newly developed uses of the analytical instrument.

Each of the informational bits referred to in the listed translations can be related to the windows 42 formed through the flange 40 on the reagent cartridge. The lowermost window, as indicated in FIG. 8, provides bit B0. In the charts, B0 determines a 1 when the window is open or uncovered by a portion of the label, and B0 determines a 0 when the window is covered by a tab portion formed on the end of the label. The remaining six windows 42 refer to bits B1 through B5 relate to windows 42 by numerically counting upwardly in FIG. 8. Thus the second window from the bottom provides bit $B_1$, the third window up from the bottom provides bit $B_2$, etc.

The disclosed informational apparatus and system provides a more reliable automated means of providing information to an analytical instrument which compliments a multi-reagent storage and delivery apparatus to substantially increase the validity of results obtained through use of the supplied chemical reagents.

What is claimed is:

1. A reagent storage and delivery apparatus for an analytical instrument performing chemical analysis, comprising:

a reagent cartridge comprising a plurality of chambers for containing fluidic reagent, each chamber having an entry port and resealable seal means for receiving a probe to withdraw reagent from the cartridge, and further comprising a flange member extending outwardly from said cartridge and including a plurality of openings formed therethrough to define windows through which an optical signal may be transmitted;

label means for cooperating with said flange member, said label means comprising an end portion selectively formed to cover selective ones of the windows of said flange member to determine a grouping of open and closed windows which may be used to define a binary code;

receiving means for receiving said reagent cartridge for operation with an analytical instrument, said receiving means defining a receiving space closely fitting the shape of said cartridge to precisely guide the cartridge for insertion into said receiving means to permit probes held by said receiving means to transfix said seal means of said cartridge to enter said entry ports for withdrawal of reagent from said cartridge; and means for reading said code defined by said cartridge and said label means, to provide information contained by said code to the analytical instrument for facilitating chemical analysis.

2. The reagent cartridge of claim 1 further comprising vent means for venting each chamber of the cartridge during withdrawal of fluid from said cartridge.

3. The reagent cartridge of claim 2 when said vent means comprises openings formed through a cap covering the top of each chamber and includes a removable tape for sealing said vent means for storage of said cartridge.

4. The apparatus of claim 1 wherein said receiving means further comprises means for ejecting a cartridge inserted therein.

5. The apparatus of claim 5 wherein said ejection means comprises lever means residing within a lower portion of said receiving space and pivotal about a pivot to engage said cartridge and force said cartridge from said receiving means.

6. The apparatus of claim 1 wherein said reading means comprises an optical array having a light source and a light detector responsive to each of said windows formed through said flange member on said cartridge, said optical array providing a signal indicating an open or a closed window for each of said windows formed through said flange member to determine a binary code from which a digital signal may be generated.

7. The apparatus of claim 6 wherein said reading means further comprises a programmable computer for generating and processing digital signals including software program means which instructs the computer to compare said digital signal generated from the binary code defined by the reagent cartridge and label means in combination, with program means information to instruct an analytical instrument to perform a select analysis.

8. A reagent storage and delivery apparatus for an analytical instrument performing chemical analysis comprising:

a reagent cartridge having an extensional portion extending outwardly from one end of said cartridge, said extensional portion having a fixed, aligned series of openings formed through said extensional portion of said cartridge to provide windows for transmission of optical signals, said windows providing an element for defining an informational code, said openings being located toward the periphery of the extensional portion;

label means initially separate from the reagent cartridge for cooperating with said extensional portion of said cartridge to define said informational code, said label means comprising a formed portion having a selected shape alignable with said extensional portion of said cartridge providing a complemental element for defining said code, said label means being attached to said cartridge with said formed portion of said label positioned to cooperate with said extensional portion of said cartridge to selectively expose or obscure said windows to define said code wherein said formed portion of said label means comprises an end portion of said label means wherein no, one or more notches are formed which cooperate with said openings formed in said cartridge extensional portion to define said code when said label means is aligned with said extensional portion.

9. A method of manufacturing a reagent storage and delivery apparatus for an analytical instrument performing chemical analysis, the method comprising the steps of:

forming a reagent cartridge having an extensional portion extending outwardly from one end of said cartridge, said extensional portion having a fixed, aligned series of openings formed through said extensional portion, said openings providing an element for defining an information code, said openings being located toward the periphery of said extensional portion;

forming separate label means for cooperating with said extensional portion of said cartridge to define said informational code, said label means comprising a formed portion having a selected shape alignable with said extensional portion of said cartridge providing a complemental element for defining said code, wherein said formed portion of said label means comprises an end portion of said label means wherein no, one or more notches are formed; and applying said label means to said extensional portion wherein said no, one or more notches cooperate with said openings formed in said cartridge extensional portion to define said code when said label means is applied to said extensional portion.

10. A method as in claim 9 wherein the step of forming the obscuring means includes forming a portion of a label alignable with said extensional portion.

11. A method as claimed in claim 9 wherein the reagent cartridge comprises a plurality of chambers for containing fluid reagent.

* * * * *